United States Patent [19]

Bove et al.

[11] Patent Number: 4,973,556

[45] Date of Patent: Nov. 27, 1990

[54] MONOCLONAL ANTIBODIES TO INTERFERON ALPHA2 AND HYBRIDOMAS PRODUCING SUCH ANTIBODIES

[75] Inventors: Sylvie Bove, Huningue; Catherine Favre, Lyons, both of France; Nick Lydon, Binningen, Switzerland

[73] Assignee: Schering Corporation, Kenilworth, N.J.

[21] Appl. No.: 248,296

[22] Filed: Sep. 21, 1988

Related U.S. Application Data

[63] Continuation of Ser. No. 703,239, Feb. 20, 1985, abandoned.

[30] Foreign Application Priority Data

Feb. 24, 1984 [FR] France .................. 8402849

[51] Int. Cl.$^5$ .................. C12N 5/12; C07K 15/28; C12Q 1/00
[52] U.S. Cl. .................. 435/240.27; 530/387; 530/413; 435/7; 935/104; 935/108; 935/110; 436/548
[58] Field of Search .............. 530/387, 388, 413, 806, 530/808; 435/7, 68, 70, 172.2, 240.27, 811, 70.21; 935/104, 106–108, 110; 436/548, 543, 815; 424/85.4, 85.7

[56] References Cited

U.S. PATENT DOCUMENTS

| | | | |
|---|---|---|---|
| 4,423,147 | 12/1983 | Secher | 435/68 |
| 4,499,014 | 2/1985 | Estis | 530/351 |
| 4,599,306 | 7/1986 | Altrock | 435/7 |
| 4,643,992 | 2/1987 | Goodman | 514/45 |

FOREIGN PATENT DOCUMENTS

| | | |
|---|---|---|
| 2492842 | of 0000 | France . |
| 2500754 | of 0000 | France . |
| 81-02899 | 10/1981 | PCT Int'l Appl. . |
| 2111527 | of 0000 | United Kingdom . |

OTHER PUBLICATIONS

Shearer, M. et al. "Monoclonal Antibodies that Distinguish Between Subspecies of Human Interferon-α and that Detect Interferon Oligomers", *J. Immunol.* 133 (6): 3096–3101, Dec. 1984.

Lydon, N. B. et al., Biochemistry, 24:4131–4141 (1985).

Arnheiter, H. et al., Nature 294(5838):278–280 (1981), cited in Chem. Abstract CA96(15):12062.

Imai, et al., "Demonstration of Two Subtypes of Human Leuocyte Interferon (IFN-α) by Monoclonal Antibodies", J. Immunol., vol. 128, No. 6: 2824–2825 (1982).

Novick, et al., "Monoclonal Antibodies to Humanα-Interferon and Their Use for Affinity Chromatography", J. Immunol., vol. 129, No. 5: 2244–2247 (1983).

Franke, et al., "Carboxyterminal Region of Hybrid Leukocyte Interferons Affects Antiviral Specificity", DNA, vol. 1, No. 3: 223–230 (1982).

Laurent et al., "Characterization of Monoclonal Antibody Specific for Human Alpha Interferon", Hybridoma, vol. 1, No. 3: 313–322 (1982).

Staehelin et al., "Monoclonal Antibodies to Human Leukocyte Interferons: Their Use in Assay and Purification", Tex. Reports Biol. Med., vol. 41: 43–58 (1981).

Adolf et al., "Production of Monoclonal Antibodies to Human IFN-α and Their Use for Analysis of the Antigenic Composition of Various Natural Interferons", J. Cell. Physiol., vol. 2: 61–68 (1982).

Mannel et al., "A Rat Monoclonal Antibody Against Mouse Alpha and Beta Interferon of All Molecular Weight Species", Nature, vol. 296, pp. 664–665 (1982).

*Primary Examiner*—Margaret Moskowitz
*Assistant Examiner*—Paula Hutzell
*Attorney, Agent, or Firm*—Anita W. Magatti; Gerald S. Rosen; Stephen I. Miller

[57] ABSTRACT

This invention relates to monoclonal antibodies to interferon alpha and to hybridomas producing such antibodies. These antibodies are preferably of the immunoglobulin subclass IgGl and preferably do not bind to alpha or alpha interferon. They can be used in assaying, purifying or isolating proteins, such as interferon alpha, for which they are specific.

6 Claims, No Drawings

MONOCLONAL ANTIBODIES TO INTERFERON ALPHA2 AND HYBRIDOMAS PRODUCING SUCH ANTIBODIES

This is a continuation of application Ser. No. 703,239 filed Feb. 20, 1985.

This invention relates to novel monoclonal antibodies to interferon α2 and to hybridomas producing such antibodies.

It is well known in the art that it is possible to obtain a cell line which is able to produce a homogeneous, i.e. monoclonal, antibody. The basic technique was originally described by Kohler and Milstein [Nature 256, (1975)] and comprises the fusion of mouse myeloma cells to spleen cells and selection of clones capable of producing the desired antibody. This general procedure has also been described in U.S. Pat. Nos. 4,364,932, 4,364,934, 4,364,935, 4,364,937 and 4,361,550.

Although the general method has been known for some years, there are in fact numerous difficulties to overcome and specific variations have to be found for each case. There is no certainty that a suitable hybridoma will be found and, equally, there is no certainty that the hybridoma will produce an antibody having the desired properties.

As is well known, antibodies are useful for various purposes. Thus monoclonal antibodies may in particular be useful for assaying (diagnostic kit) or for isolation and purification of the proteins for which they are specific. (See for example PCT/GB 81/00239, Publication No. W082/01773).

The PCT patent application number PCT/GB81/00067 as well as "J. Gen. Virol. (1981) 53, 257-265" describe a monoclonal antibody, NK2, which is specific to α-interferons in general and does not bind to other interferons, e.g. β-interferon etc. The term α-interferon or leukocyte interferon, however, covers a group of 15 or more distinct molecular entities and the antibodies of this invention are clearly different from NK2 in that they are of different Ig subclass and will bind to different α-interferon entities.

More recent research has made it possible to isolate single species from the group of α-interferons, to produce each species in larger quantities and to purify it to a homogeneous compound.

One of these α-interferons called interferon $\alpha_2$ (IFNα$_2$) has in various tests proved to be a most promising pharmaceutically active substance useful for combatting various diseases. IFNα$_2$ is widely described in literature and may be obtained either by isolation from blood samples or by so-called recombinant DNA technology, e.g. as described in the published European Patent Application No. 0032134.

It is obvious that it is highly desirable to have antibodies which are specific to IFNα$_2$ only and which do not bind to other closely related α-interferons or to β-interferon etc.

The purpose of this invention therefore was to isolate monoclonal hybridomas which are able to produce monoclonal antibodies binding strongly to IFNα$_2$ and not or only weakly to other α-interferons.

As mentioned above, such antibodies are highly useful for various purposes, e.g. for assaying or purifying (affirmative chromatography) IFNα$_2$. A further possible use is for isolation of shorter interferon α$_2$-type protein molecules, e.g. portions of IFNα$_2$, which, though smaller than the original IFNα$_2$-molecule, still have the same or similar characteristics and activities as IFNα$_2$ for a particular molecular structure and, accordingly, respond to invasions of foreign molecules into the mammalian body.

The hybridomas and the antibodies of this invention may be obtained by the following procedure:

1. Mice are immunized with several injections of IFNα$_2$. The type of mice used is not critical but good results are achieved with Balb/c females. The antigen (IFNα$_2$) may be applied in any suitable form, e.g. in complete Freund Adjuvant (CFA) emulsified with phosphate buffered saline (PBS) (ratio 1:1). The number of injections and the quantity of antigen administered must be such, that useful quantities of suitably primed splenocytes are produced. Usually, immunization consists of three intraperitoneal injections with 10 µg of antigen at about 2-week intervals. This is followed by a further boost consisting of 10 µg antigen in PBS Intraveneously and 10 µg antigen in CFA/PBS Intraperitoneally.

2. The spleens of the immunized mice are removed and spleen suspensions are prepared. This procedure follows well known techniques.

3. The spleen cells are fused with mouse myeloma cells. The technique for fusing myeloma cells with spleen cells is well known. Most preferably the fusion is achieved by heating a mixture of the two cell types with certain chemical ingredients (fusion promoter), e.g. polyethyleneglycol (PEG) having an average molecular weight from about 1000 to 4000 (PEG1000). Several mouse myeloma cell lines are known and easily available. Preferred are cell lines which are HGPRT-deficient (HGPRT=Hypoxanthine Guanosyl Phosphoribosyl Transferase) and accordingly will not survive in HAT (culture medium comprising hypoxynthine, aminopterine and thymidine). Preferably the myeloma cell line used should be of the non-secreting type in that it does not itself produce any antibody. A suitable cell line for the purpose of this invention is the so-called NS1 cell line. These cells were derived from P3/X63-A8 myeloma cells by Köhler and Milstein.

4. The fused spleen cells are cultured in several separate containers. Also this step follows standard procedures. The cell cultures obtained in step 3 are mixtures of fused spleen cells, unfused spleen cells and unfused myeloma cells. Preferably the cultivation is carried out in a medium which will eliminate the unfused myeloma cell line, e.g. in a HAT medium. Those unfused spleen cells which are non-malignant will normally stop growing after a short period of time, whereas the fused cells, which are HGPRT+ can grow in HAT medium.

5. The supernatants of the hybridoma cells in each container are tested for the presence of IFNα$_2$-antibodies. This test may conveniently be carried out by applying an enzyme linked immunosorbant assay (ELISA). In the present case antibodies linked to the enzyme alkaline phosphatase were chosen, but also other procedures are conceivable.

6. Hybridomas producing the desired antibodies are selected and cloned. The cloning is preferably carried out using the limiting dilution technique.

7. The desired antibodies are produced by means of the selected hybridomas. This production may be achieved in vitro by culturing the hybridoma in a suitable medium followed by isolation of the antibody, however, this method may not yield sufficient quantities.

A preferred method for producing larger quantities of antibody uses an in vivo approach. The hybridoma is injected back into mice where it will cause production of ascites fluid containing substantial quantities of the desired antibody which is then isolated according to standard procedures.

According to the present invention there are provided hybridomas capable of producing antibodies against interferon $\alpha_2$; methods for producing the antibodies, and methods and compositions for utilizing these antibodies.

Although only a relatively small number of hybridomas producing antibodies against $\alpha_2$ interferon are described, it is contemplated that the present invention encompasses all monoclonal antibodies exhibiting the characteristics described herein.

Further included within the subject invention are methods for preparing the monoclonal antibodies described above employing the hybridoma technique illustrated herein. Although only limited examples of hybridomas are given herein, it is contemplated that one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having the reactivity characteristics described above are included within the subject invention, as are methods for making this antibody employing the hybridoma.

Further aspects of the invention are methods of treatment or diagnosis employing the monoclonal antibodies exhibiting the pattern of reactivity provided herein.

EXAMPLE 1. Immunization of Mice

Balb/C female mice were immunized by three injections at fifteen days intervals with 10 μg of IFN$\alpha_2$ (Schering-Plough Corporation) in CFA/PBS emulsion (1:1). A total volume of 0.2 ml was injected intraperitoneally into each mouse. Fifteen days after the third injection a boost was made by injecting 10 μg of antigen in CFA intraperitoneally and at the same time 10 μg of antigen in PBS intravenously. Four days after the last injection the mice were bled and their spleen excised for fusion.

2. Cell Fusion

The spleen was suspended in PBS ($Ca^{++}$- and $Mg^{++}$-free) and a cell count was carried out (one spleen comprises approximately $10^8$ cells).

After filtration through sterile gauze, the cells were washed twice in cold $Ca^{++}$- and $Mg^{++}$-free PBS (GIBCO CAT 420). The mouse myeloma cells (NS1) were washed (3 times with the same type PBS) and the two cell types were mixed and centrifuged together. The mixture comprised $\sim 10^8$ spleen cells and $\sim 10^7$ NS1 cells.

About 0.2 ml of supernatant was left over the cells. After disrupting the pellet by gentle agitation of the tube, 1 ml of PEG 1000 (Merck Art. 9729), 50% in PBS without $Ca^{++}$ and $Mg^{++}$, was added dropwise during 1 mn with constant agitation at 37° C. After thirty seconds of agitation at 37° C., the tube was filled slowly with warm PBS without $Ca^{++}$ and $Mg^{+}$ and centrifuged. The cells were then directly re-suspended in HAT Medium and distributed into 24 well plates (1 ml per well with about $2 \times 10^6$ cells per well). At this stage, non-treated splenocytes (1:10 of each spleen) were added as feeder cells.

3. Culture of the Hybridoma Cells 24 hours after the fusion, 1 ml of HAT medium was added to each well. Fresh medium was added three times a week to all the wells. The selection was achieved by culturing the hybridomas in HAT Medium during 3 weeks followed by culturing the cells during three subsequent weeks in HT medium (same medium but without aminopterine) and then kept in normal culture medium (RPMi 1640 with 10% FCS).

As soon as possible, the hybridoma cells were frozen using standard techniques. The supernatant was kept and tested for the presence of anti-IFN$\alpha_2$ antibodies.

4. Test (screening) For Presence Of Anti-IFN$\alpha_2$ Antibodies

The presence of anti-IFN$\alpha_2$ antibodies in the supernatants of the hybridoma cell cultures was tested by an enzyme linked immunosorbant assay (ELISA). The use of antibodies linked to the enzyme alkaline phosphatase following classical techniques (see "Enzyme Linked Immunorsorbant Assay"; A. Voller, D. Bidwelland, A. Bartlett; Manual of Clinical Immunology, chapter 45, p. 359) was chosen and adapted for detection of monoclonal anti-IFN$\alpha_2$ antibodies. The test used comprised the following steps:

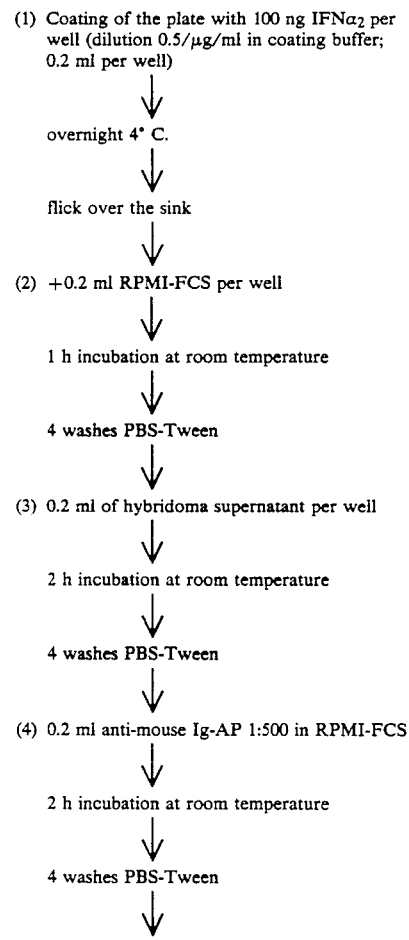

(5) 0.2 ml PNPP in diethanolamine buffer

↓ readings after 15 mn, 30 mn, 45 mn, 1 h.

The absorption of IFNα₂ to the bottom of the plates (96 well plates; NUNC Immune plate I CAT No. 2-39454) was performed in coating buffer (carbonate-bicarbonate buffer) containing 1.59 g Na$_2$CO$_3$, 2.93 g Na HCO$_3$, 0.2 g NaN$_3$ per liter of distilled water. After one night at 4° C., the wells were saturated with protein by an incubation of 1 hour at room temperature with the culture medium containing RPMi-10% FCS (0.2 ml per well).

The plate was then washed four times with PBS-Tween containing 8 g NaCl, 0.2 g KH$_2$PO$_4$, 2.9 g Na$_2$HPO$_4$ (12 H$_2$O), 0.2 g KCl, 0.5 ml Tween 20 in one liter distilled water (pH 7.4).

After incubation of the plate with hybridoma supernatants, the presence of mouse anti-IFNα$_2$ antibodies was revealed by sheep anti-mouse immunoglobulins conjugated with alkaline phosphatase (e.g. NEI-500 from NEN).

After two hours of incubation with the conjugate and four subsequent washings, 0.2 ml of substrate solution was added. The substrate (paranitrophenyl phosphate; PNPP Sigma 104 phosphatase substrate ref.: 104–105) was dissolved (1 tablet of 5 mg for 5 ml of buffer) in a buffer containing 100 mg of MgCl$_2$·(6H$_2$O) ; 0.2 g NaN$_3$, 97 ml diethanolamine in one liter distilled water (pH 9.8, adjusted with HCl). The optical density at 405 nm was read at different time intervals after addition of substrate (Autoreader MR580 from Dynatech). Strong positive hybridomas were selected for cloning. These were designated 6N5, 7N2 and 7N4.

5. Cloning

The cloning of the hybridoma cells was performed by the limiting dilution technique.

Hybrid cells were diluted in the culture medium and distributed into 96 well plates (flat bottom linbro 76003-05) in order to have 60 cells per plate (0.2 ml per well). Peritoneal macrophages of Balb/C mice were used as feeder cells; these were collected by washing the peritoneal cavity of mice with HBSS (GIBCO Cat. No. 406) containing 1% of antibiotics (Penicilline-Streptomycine) at 4° C. Usually the peritoneal macrophages recovered from one mouse were sufficient for one 96 well plate (about 2 to 4×10$^5$ cells per well).

After about three weeks, the clones could be seen by eye. They were then transferred to 24 well plates. At this stage the clones were frozen as quickly as possible. The supernatants were then kept and tested for anti-IFNα$_2$ activity.

The hybridoma 6N5 gave one active clone which designated 6N5-2-I. Hybridoma 7N2 gave one active clone which was designated 7N2-4. Hybridoma 7N4 produced one active clone which was designated 7N4-1. The monoclonal antibodies produced by the active hybridomas were designated A6N5-2-I, A7N2-4 and A7N4-1. The monoclonal hybridomas were deposited in the "COLLECTION NATIONALE DE CULTURE DE MICROORGANISMES" at "INSTITUT PASTEUR", 28, rue du Docteur Roux, 757 Paris Cedex 15, France on Feb. 22, 1984 where they received the deposition numbers I-279 (6N5-2-I), I-278 (7N2-4) and I-277 (7N4-1).

6. Production of Ascites Fluid

In order to obtain large amounts of monoclonal antibodies, ascites fluid was induced in Balb/C mice by injecting hybridoma cells.

Four days before injection of the cells the mice were treated i.p. with 0.5 ml of pristane (2,6,10,14-Tetramethyl-penta-decane Aldrich T22802). After three washes of hybridoma cells with PBS Dulbecco (GIBCO 041.4040), the cell suspension was adjusted to 2.5×10$^7$ cells per ml and 0.2 ml injected into each mouse (5×10$^6$ cells per mouse). After a period ranging from ten to twenty days, the ascitic fluid could be collected. After a period of a few days of rest it was possible to collect ascitic fluid from the same mice again. At least two or three samples of ascitic fluid were harvested from each mouse.

7. Isolation and Purification Of the Clones From Ascites Fluids

Ammonium sulfate precipitation : 27 ml of ascites fluid was diluted four-fold in cold PBS and placed on ice. An equal volume of saturated (NH$_4$)$_2$SO$_4$ solution (4° C.) was added slowly with stirring over a period of several minutes: final (NH$_4$)$_2$SO$_4$ concentration was 50% saturation. The solution was left on ice for 30 min. Centrifugation was at 5000 ×g for 10–15 mn. The pellet was recovered and dissolved in 15 ml of buffer containing 40 mM-NaCl, 20 mM-Tris/HCl, pH 7.8 (buffer A). The re-suspended pellet was dialysed against 100 volumes of buffer containing 20 mM-NaCl, 20mM-Tris/HCl, pH 7.8 (buffer B). Prior to ion exchange chromatography denatured protein was removed by centrifugation at 15,000×g for 10 min.

DEAE cellulose chromatography : DE 52 (Whatman), which had been equilibrated in buffer B, was packed into a column (2.5 cm×27 cm) giving a packed bed volume of 132 ml. Packing was carried out with a pumped flow rate of 45 ml/hr/cm. Chromatography was performed at room temperature. Immediately prior to loading, the dialysed sample was adjusted so as to constitute the ionic conditions of buffer B. The sample was loaded at a flow rate of 2 ml/min. After washing with buffer B (1/10 of bed volume) the column was eluted with a linear gradient of NaCl (40 mM–200 mM). The total gradient volume was 1 liter. The elution flow rate was 50 ml/hr. 10 ml fractions of eluate were collected.

8. Lyophylisation

Eluate fractions were dialysed against 1% (w/v) N$_4$HCO$_3$ for 48 hrs. The final volume following dialysis was 168 ml. The pool was sterilized by filtration through a 0.22 Micron membrane filter (Falcon). 10 ml aliquots of filtrate were transferred into sterile bottles and lyophilised. Sterile conditions were maintained following lyophilisation by using an automatic capping device.

CHARACTERIZATION OF THE 5 ANTI-INTERFERONα$_2$ ANTIBODIES A6N5-2-I, A6N5-2-II, A7N2-4 and A7N4-1

The characterization of a monoclonal antibody should provide the following information:
  (i). Determination of the specificity, i.e. to which type of interferons will the antibody bind.

(ii). Determination of Ig subclass.
(iii). Determination of the effect the antibody has on biological functions of the molecule (in this case interferons).

1. Specificity of the monoclonal antibodies determined by using the ELISA test

The specificity was determined by using the ELISA test described under item 4 of the Example above.

2. Determination of Ig subclass

The isotype of the monoclonal antibodies purified from ascites fluid was tested by an indirect ELISA test. The plates were coated with 100 ng IFN$\alpha_2$ per well and treated with RPMI-10% FCS as already described. The monoclonal antibodies diluted in RPMI-10% were allowed to fix to the antigen coated at the bottom during 2h incubation. The wells were then filled with a solution of antibodies directed against various mouse Ig subclasses (dilution 1:1000). All the anti-isotypes used here were produced in rabbits. (IgM; IgG$_1$; IgG 2a; IgG 2b; IgG 3; IGA, $\Lambda$ and K). The presence of anti-isotype antibodies was detected by anti rabbit Ig conjugated to alkaline phosphatase. The conditions of incubation and the reading of the results were as described for the ELISA test above.

3. Functional Tests

A. Inhibition of 2'–5' oligo (A) synthetase

Treatment of cells with IFN$\alpha_2$ results in the induction of 2'–5' oligo (A) synthetase. This activity was used as a functional test for IFN$\alpha_2$, i.e. it was determined whether the antibodies inhibit the induction of the 2'–5' oligo (A) synthetase by IFN$\alpha_2$.

In addition to its anti-viral actions, IFN$\alpha_2$-treatment of cells have been shown to induce various mRNA's and proteins. Among the proteins induced are a number of enzymes, including 2'–5' oligo (A) synthetase. 2'–5' oligo (A) synthetase is activated by dsRNA [e.g. poly (I). (C)] and produces a heterogeneous family of 2'–5' linked oligoadenylates of which the di-, tri- and tetra-adenylates are the most abundant. Induction of 2'–5' oligo (A) synthetase can be utilized as a reliable marker for the biological activity of interferons. The Hela S$_3$ cell line was used to investigate the effects of interferon preparations on 2'–5' oligo (A) synthetase induction. The effect was measured by determining the quantities of 2'–5' oligo (A) produced.

This 2'–5' oligo (A) synthetase test includes the following steps:

(a) pre-treatment of INF$\alpha_2$ with the monoclonal antibody;
(b) addition of the immune complex obtained to HeLa S$_3$ cell cultures; and
(c) assaying HeLa S$_3$ cell extracts from cultures (b) for 2'–5' oligo (A) synthetase activity.

Step (a): To 5 ml of monoclonal culture supernatant was added 100 ng INF$\alpha_2$ per ml. The mixture was subjected to a one hour incubation at 37° C.

Step (b): 2.5 ml of media obtained according to step (a) were added to HeLa S$_3$ cell cultures containing 7.5 ml of fresh media (RPMI+10% CFS), mixed by shaking and incubated for 20 hours at 37° C., in a humidified CO$_2$ incubator.

Step (c): Following washing in PBS, adherent HeLa cells were scraped from plates into 2 ml of PBS (0.01 M-phosphate buffer, pH 7.2, 0.15 M-NaCl). Plates were then washed with an additional 1 ml of PBS. Cells were pelleted at 500×g for 5 minutes at room temperature. The supernatant liquid was carefully removed using a Pasteur pipette. The pellet was then resuspended in lysis buffer containing 10 mM-KCl, 1.5 mM magnesium acetate, 0.5%-Triton X-100 and 20 mM-Hepes/KOH, pH 7.5. Cells were lysed by treating at 4° C. for 10 minutes. The lysate was immediately centrifuged at 30,000 Xg for 15 minutes. The supernatant material was recovered and is referred to as the HeLa S$_3$ cell extract. Extracts were subsequently assayed for 2'–5' oligo (A) synthetase activity.

The assays contained, in a final volume of 50μl: 30 μl of cell extract, 5 mM-ATP, 25 mM-Mg (OAC)$_2$, 4 mM-Fructose 1,6 diphosphate, 1 mM-DTT, 100 mM-KOAC, 20 mM-Hepes/KOH, pH 7.6, 10%-glycerol and 100 μg/ml poly (I).(C) (Miles Laboratories). Incubations were at 30° C., for 1 hour and were terminated by heating at 100° C., for 3 minutes. 2'–5' oligo (A) produced was isolated by ion exchange chromatography on DEAE- cellulose. The samples were diluted with 1 ml of buffer containing 90 mM-KCl, 20 mM-Tris-HCl pH 7.6 (start buffer). Diluted samples were passed three times over a column containing 0.5 ml of packed DE 52 (Whatman), equilibrated with start buffer. Columns were washed with 10 ml of start buffer, then eluted with 1 ml of elution buffer (350 mM-KCl 20 mM-Tris-HCl pH 7.6).

The production of 2'–5' oligo (A) was measured spectrophotometrically at 259 nm.

B. Antiproliferation

A further characteristic of the antibodies is whether they inhibit the antiproliferative effect of IFN$\alpha_2$. The test was carried out using the Daudi Cell line (obtained from the American Type Culture Collection) which is extremely sensitive to the antiproliferative action of interferons.

IFN$\alpha_2$ was incubated with monoclonal antibody for 30 mn at 37° C., in a final volume of 50 μl. This was carried out in microtiter culture plates. 100 μl of cell suspension containing 10$^4$ cells was then added to each well. After 3 days incubation in a CO$_2$ incubator, proliferation was measured by a rapid quantitative colorimetric assay.

Three hours before the end of the assay, MTT (3-[4,5-Dimethylthiazol-2-yl]-2,5 diphenyl tetrazolium bromide; 10μl of 5 mg/ml solutions) was added to each well. The microtitre culture plate was then incubated for a further 3 hours. Trays were removed from the incubator and 200 μl of 0.04 N HCl in isopropanol was added to each well. After mixing, the trays were read on a Dynatech MR 580 autoreader using a reference wavelength of 630 nm and a test wavelength of 570 nm. The blue formazan reaction product is a quantitative measure of live cell number.

The specificity test as well as the results of tests A and B above with regard to the monoclonal antibodies of this invention and of NK-2 are given in the table below.

| Monoclonal | IG-Subclass | Specificity tests | | | | | | | Functional tests | |
|---|---|---|---|---|---|---|---|---|---|---|
| | | $\alpha_2$ | $\alpha_1$ | $\alpha_7$ | $\beta$ | 30-G | 30-E | 30-D | 2'-5' oligo(A) | Anti-proliferation |
| A6N5-2-I | IgG1 | ++ | − | − | − | + | − | − | ND | ND |
| A7N2-4 | IgG1 | ++ | − | − | − | + | − | − | no | no |
| A7N4-1 | IgG1 | ++ | − | ± | − | − | − | − | yes | yes |
| NK-2 | IgG2a | ++ | − | − | − | + | − | − | yes | yes |

ND: Not Determined
++: strong positive
+: positive
−: negative

The Amino acid sequence of Interferon $\alpha_2$

CYS-ASP-LEU-PRO-GLN-THR-HIS-SER-LEU-GLY-SER-ARG-ARG-THR-LEU-MET-LEU-LEU-
ALA-GLN-MET-ARG-ARG-ILE-SER-LEU-PHE-SER-CYS-LEU-LYS-ASP-ARG-HIS-ASP-PHE-GLY-PHE-PRO-GLN-GLU-GLU-PHE-GLY-ASN-GLN-PHE-GLN-LYS-ALA-GLU-THR-ILE-PRO-
VAL-LEU-HIS-GLU-MET-ILE-GLN-GLN-ILE-PHE-ASN-LEU-PHE-SER-THR-LYS-ASP-SER-SER-ALA-ALA-TRP-ASP-GLU-THR-LEU-LEU-ASP-LYS-PHE-TYR-THR-GLU-LEU-TYR-GLN-
GLN-LEU-ASN-ASP-LEU-GLU-ALA-CAS-VAL-ILE-GLN-GLY-VAL-GLY-VAL-THR-GLU-THR-
PRO-LEU-MET-LYS-GLU-ASP-SER-ILE-LEU-ALA-VAL-ARG-LYS-TYR-PHE-GLN-ARG-ILE-
THR-LEU-TYR-LEU-LYS-GLU-LYS-LYS-TYR-SER-PRO-CYS-ALA-TRP-GLU-VAL-VAL-ARG-
ALA-GLU-ILE-MET-ARG-SER-PHE-SER-LEU-SER-THR-ASN-LEU-GLN-GLU-SER-LEU-ARG-
SER-LYS-GLU

Amino acids of the interferon $\alpha_2$-fragments 30-G: 30-E and 30-D:

| Fragment | Amino acids |
|---|---|
| 30-G | $Cys^1$ ... $Leu^{15}$—Hser |
| 30-E | $Ile^{60}$ ... $Cys^{98}$ ... $Leu^{110}$—Hser<br>$Arg^{22}$ ... $Cys^{29}$ ... $Glu^{58}$—Hser |
| 30-D | $Lys^{112}$ ... $Cys^{138}$ ... $Ile^{147}$—Hser<br>$Arg^{149}$—$Glu^{165}$ |

As can be seen the antibodies of this invention are all of the Ig subclass IgG1 whereas NK2 is of the subclass IgG2a. The antibodies A6N5-2-I and A7N2-4 do not bind to $\alpha_1$ and $\alpha_7$. All antibodies bind strongly to $\alpha_2$. NK2 binds to $\alpha_2$ and $\alpha_7$. None of the antibodies bind to $\beta$-interferon.

The substances used in the above tests are either known or their structure is given below. The sequences of $\alpha_1$ and $\alpha_7$ have been published, e.g. in:

Weissmann et al (1982): "Structure and expression of Human Alpha interferon Genes" (Interferons, pp 295, Academic Press);

Scientific American, Vol. 249 No. 2, pp 28–36, (S. Pestka).

We claim:

1. Monoclonal antibodies of the immunoglobulin subclass IgG1 which
   (a) specifically bind to interferon-alpha$_2$ and
   (b) do not bind to interferon $\alpha_1$.

2. An antibody according to claim 1 which does not bind to interferon $\alpha_7$ and is A6N5-2-I.

3. An antibody according to claim 1 which:
   (a) does not bind to interferon $\alpha_7$;
   (b) does not inhibit 2'-5' oligo (A) synthetase induction by interferon $\alpha_2$;
   (c) does not inhibit the antiproliferative effect of interferon $\alpha_2$;
   (d) is A7N2-4.

4. An antibody according to claim 1 which:
   (a) inhibits 2'-5' oligo (A) synthetase induction by interferon $\alpha_2$;
   (b) inhibits the antiproliferative effect of interferon $\alpha_2$; and
   (c) is A7N4-1.

5. Monoclonal hybridoma cell lines 6N5-2-1 Institut Pasteur accession number I-279, 7N2-4, Institut Pasteur accession number I-278 and 7N4-1, Institut Pasteur accession number I-277.

6. A continuous cell line which produces antibodies which specifically bind to interferon $\alpha_2$ but not to interferon $\alpha_1$, comprising: a stable fused cell hybrid of a mouse splenocyte immunized by human interferon $\alpha_2$ and a mouse myeloma cell.

* * * * *